(12) United States Patent
Geisberger et al.

(10) Patent No.: US 6,169,196 B1
(45) Date of Patent: Jan. 2, 2001

(54) PROCESS FOR THE PREPARATION OF ALKYLSILANES WITH BULKY ALKYL RADICALS

(75) Inventors: Gilbert Geisberger, Altötting; Tassilo Lindner, Mehring-Öd; Rudolf Reitmeier, Burghausen, all of (DE)

(73) Assignee: Wacker-Chemie GmbH, Munich (DE)

( * ) Notice: Under 35 U.S.C. 154(b), the term of this patent shall be extended for 0 days.

(21) Appl. No.: 09/493,396

(22) Filed: Jan. 28, 2000

(30) Foreign Application Priority Data

Feb. 11, 1999 (DE) .............................................. 199 05 752

(51) Int. Cl.⁷ ...................................................... C07F 7/08
(52) U.S. Cl. .................................................................. 556/479
(58) Field of Search ............................................... 512/479

(56) References Cited

U.S. PATENT DOCUMENTS

| | | | | |
|---|---|---|---|---|
| 4,469,881 | * | 9/1984 | Arkles | 556/479 X |
| 4,579,965 | * | 4/1986 | Kanner et al. | 556/479 |
| 5,082,962 | * | 1/1992 | Schilling | 556/479 |
| 5,663,400 | | 9/1997 | Reitmeier et al. | |

FOREIGN PATENT DOCUMENTS 0 602 922    6/1994   (EP) .

* cited by examiner

*Primary Examiner*—Paul F. Shaver
(74) *Attorney, Agent, or Firm*—Brooks & Kushman P.C.

(57) ABSTRACT

A process for the preparation of di- and trialkylsilanes of the general formula (I)

$$R_a R^1_b SiX_c \qquad (I),$$

in which
mono- or dialkylsilanes of the general formula (II)

$$R^1_b SiH_a X_c \qquad (II)$$

are reacted with alkenes A which have at least 3 carbon atoms and are optionally substituted by fluorine, chlorine or bromine atoms or cyano groups, in the presence of a transition metal catalyst and a trihalogenosilane of the general formula (III)

$$R^2 SiY_3 \qquad (III)$$

as an activator,
wherein, in the above general formulae (I) to (III),

R is a branched or cyclic hydrocarbon radical having at least 3 carbon atoms, optionally substituted by fluorine, chlorine, or bromine, or cyano groups, $R^1$ is an alkyl radical optionally substituted by fluorine, chlorine, or bromine, or cyano groups, $R^2$ is a hydrogen atom, or an alkyl radical optionally substituted by fluorine, chlorine, or bromine, or cyano groups, X is fluorine, chlorine, or bromine, or an alkoxy radical having 1 to 18 carbon atoms optionally substituted by fluorine, chlorine, or bromine, or cyano groups, Y is fluorine, chlorine or bromine, a is 1 or 2, b is 1 or 2, and c is 1 or 2.

17 Claims, No Drawings

PROCESS FOR THE PREPARATION OF ALKYLSILANES WITH BULKY ALKYL RADICALS

TECHNICAL FIELD

The invention relates to a process for the preparation of di- and trialkylsilanes with bulky alkyl radicals by hydrosilylation of hydrogen-containing silanes with alkenes in the presence of a transition metal catalyst and an activator.

BACKGROUND ART

Dialkyldialkoxysilanes with bulky alkyl radicals on the silicon are now sought after, for example, by almost all major producers of polypropylene for their latest generation Ziegler catalysts. Silanes with short-chain, branched alkyl and cycloalkyl groups are in particular demand. These silanes must be employed in a high purity. Until a short time ago, these silanes were produced industrially exclusively from chlorosilanes or alkoxysilanes by the expensive organometallic route, that is to say employing large amounts of both solvents, and metals such as sodium or magnesium. Accordingly it was necessary to dispose of large amounts of metal-containing by-products.

Alkyl- or dialkylsilanes which, in addition to hydrogen bonded directly to silicon, contain chlorine atoms and/or alkoxy radicals, satisfactorily hydrosilylate linear alkenes having a terminal double bond, so-called α-olefins, only in the presence of noble metal catalysts. Thus, for example, the hydrosilylation of silanes such as dichlorosilane, which contain 2 hydrogen atoms bonded directly to silicon, with branched or cyclic alkenes containing at least 3 carbons, leads only to a monoalkylchlorosilane, even if alkene is present in excess.

U.S. Pat. No. 5,663,400 describes a hydrosilylation process for the preparation of di- and trialkylsilanes with bulky alkyl radicals wherein the hydrosilylation of hydrogen-containing silanes takes place with bulky alkenes in the presence of a transition metal catalyst and activators. Hydrocarbons which contain aldehyde, keto or epoxide groups or halogen atoms as functional groups are employed as activators. Many different by-products, some of which are difficult to separate, are formed in this process. As a result, it is difficult to obtain highly pure products.

DISCLOSURE OF INVENTION

An object of the present invention is to provide a process for the preparation of di- and trialkylsilanes in which at least one alkyl radical is branched or cyclic or contains at least 3 carbons, and preferably the silanes also contain chlorine atoms and/or alkoxy radicals, during which process only few by-products, by-products which are easy to separate, are formed.

BEST MODE FOR CARRYING OUT THE INVENTION

The invention relates to a process for the preparation of di- and trialkylsilanes of the general formula (I)

  (I), in which
mono- or dialkylsilanes of the general formula (II)

  (II)

are reacted with alkenes A having at least 3 carbon atoms, which are optionally substituted by fluorine, chlorine or bromine atoms or cyano groups, in the presence of a transition metal catalyst and a trihalogenosilane of the general formula (III)

  (III)

as an activator, wherein, in the above general formulae (I) to (III),

R is a branched or cyclic hydrocarbon radical having at least 3 carbon atoms, optionally substituted by fluorine, chlorine, or bromine atoms, or cyano groups, $R^1$ is an alkyl radical, optionally substituted by fluorine, chlorine or bromine atoms or cyano groups, $R^2$ is a hydrogen atom, or an alkyl radical optionally substituted by fluorine, chlorine, or bromine atoms, or cyano groups, X is fluorine, chlorine or bromine, or an alkoxy radical which has 1 to 18 carbon atoms, optionally substituted by fluorine, chlorine, or bromine atoms, or cyano groups, Y is fluorine, chlorine or bromine, a is 1 or 2, b is 1 or 2, and c is 1 or 2.

In the above general formulae (I) and (II), the sum of a, b and c is 4.

Fewer by-products, which are easier to separate off, are formed in the process than in the known hydrosilylation processes for the preparation of di- and trialkylsilanes of the general formula (I). In particular, no activators which contain functional groups which are not present in the hydrosilylation process and can additionally form further by-products are fed to the process.

The above reaction is particularly important for the addition of alkenes A which are sterically bulky, that is to say branched or cyclic. However, linear alkenes having from 5 carbon atoms upward are also hydrosilylated particularly poorly without an activator. In particular, alkenes having up to 18 carbon atoms may be routinely used according to the invention. The alkenes A can have one or more unsaturated C=C bonds in the molecule.

Examples of the sterically bulky alkenes A are cyclopentene, cyclohexene, cyclobutene, cyclooctene, cyclopentadiene, norbornene (bicycloheptene), cyclooctadiene, cyclohexadiene, 3-methylcyclopentene, 3-methylcyclopentadiene, isobutene, 2,3-dimethyl-1-butene, 2,3-dimethyl-2-butene, 3,3-dimethylbutene, 2,4,4-trimethyl-1-pentene (diisobutylene) or 4-methylene-2,2,6,6-tetramethylheptane (triisobutylene).

The radical R is formed by addition of the alkene A onto the Si-H group in the silane of the general formula (II).

The radical $R^1$ preferably has not more than 18, in particular not more than 6 carbon atoms. Preferred examples of the alkyl radicals $R^1$ are the methyl, ethyl, n-propyl, isopropyl, n-butyl, isobutyl, sec-butyl, tert-butyl, n-pentyl, isopentyl, neopentyl and tert-pentyl radicals; hexyl radicals such as the n-hexyl, 2,3-dimethylbutyl and 3,3-dimethylbutyl radicals; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; and cycloalkyl radicals such as cyclopentyl, cyclohexyl, cycloheptyl, cyclooctyl and norbornyl radicals and methylcyclohexyl radicals.

Examples of substituted radicals $R^1$ are cyanoalkyl radicals, such as the β-cyanoethyl radical, and halogenated alkyl radicals, such as the 3,3,3-trifluoro-n-propyl radical, the 2,2,2,2',2',2'-hexafluoroisopropyl radical and the heptafluoroisopropyl radical.

Preferred radicals X are alkoxy radicals having 1 to 6 carbon atoms such as the methoxy, ethoxy, n-propoxy, isopropoxy, n-butoxy, isobutoxy, sec-butoxy and tert-butoxy radicals; pentyloxy radicals such as the n-pentyloxy radical, and hexyloxy radicals such as the n-hexyloxy radical, these radicals optionally substituted by fluorine, chlorine, or bromine atoms, or by cyano groups. The methoxy and ethoxy radicals are particularly preferred. The unsubstituted alkoxy radicals are preferred. The chlorine atom is preferred when X is a halogen atom.

The radical $R^2$ preferably has not more than 18, in particular not more than 6 carbon atoms. Preferred examples of the hydrocarbon radicals $R^2$ are the alkyl and alkenyl radicals mentioned for $R^1$, and also aryl radicals such as the phenyl, naphthyl, anthryl and phenanthryl radicals; alkaryl radicals such as o-, m- and p-tolyl radicals, xylyl radicals and ethylphenyl radicals; and aralkyl radicals such as the benzyl radical and the α- and the β-phenylethyl radicals.

Preferred examples of substituted radicals $R^2$ are the substituted alkyl and alkenyl radicals mentioned for $R^1$, and also halogenoaryl radicals, such as the o-, m- and p-chlorophenyl radicals.

Preferred activators are $C_1$- to $C_6$-alkyltrichlorosilanes, such as methyltrichlorosilane, propyltrichlorosilane, cyclopentyltrichlorosilane and trichlorosilane. The chlorine atom is preferred as the halogen atom Y. The amount of activator (s) to be used is preferably 0.5–30% by weight, in particular 5–15% by weight of the total mixture.

The usual hydrosilylation catalysts can in principle be used as the transition metal catalysts. Elements and compounds of rhodium and, in particular, of platinum are particularly suitable. Preferred rhodium complexes are $RhCl_3/PPh_3$ excess, $ClRh(PPh_3)_3$ (Wilkinson catalyst) and $HRh(CO)(PPh_3)_2$.

The platinum catalysts are, for example, solutions of hexachloroplatinic acid or $H_2PtCl_6.6\ H_2O$ in alcohols such as isopropanol (Speier catalyst), olefin complexes such as Karstedt catalyst ($Pt_2(ViMe_2SiOSiMe_2Vi)_3$), or phosphine complexes such as $Cl_2Pt(PPh_3)_2$. Platinum can also be deposited on solid support materials, such as active charcoal, aluminum oxide or silica gel. The preferred hydrosilylation catalyst is hexachloroplatinic acid/isopropanol or dilutions thereof, for example in cyclopentene or in inert solvents, such as hydrocarbon solvents.

Transition metal catalysts are preferably employed in a concentration of $10^{-6}$ to $10^{-2}$ mol, in particular $10^{-5}$ to $10^{-3}$ mol of catalyst per mole of silane of the general formula (I) or approximately, 2–300 mg of platinum per mole of silane of the general formula (I). For economic reasons, an amount of catalyst of 10–100 mg of Pt/mol of silane is particularly preferred. Depending on the temperature program, a considerable amount of this catalyst can be reused by recycling the soluble Pt content after removal of the products, for example via molecular distillation.

The reaction temperature can be varied over a very wide range. The optimum temperature depends primarily on the reactants, in particular on the alkene A and the catalyst concentration. The temperature is preferably 30 to 190° C., in particular 70 to 150° C., since the risk of accumulation of reaction energy and decomposition of the catalyst, or of the ignition point of the reaction mixture being reached is largely avoided.

Preferably, somewhat more than 1 mol of alkene A is employed per mole of the mono- and dialkylsilanes of the general formula (II). A slight excess of alkene A of at least 2%, in particular 1.05–1.5 mol, preferably 1.1–1.3 mol per mole of silane of the general formula (II) is preferably employed.

Since the reaction overall is severely exothermic, it is advisable in batch operation to initially introduce the activator into the reaction vessel and to meter in at least one component continuously during the reaction and thus to keep the internal temperature virtually constant.

For the preparation of the mono- and dialkylsilanes of the general formula (II), wherein radicals $R^1$ contain at least 2 carbon atoms, silanes of the general formula (IV)

$$R^1_{b-1}SiH_eX_c \qquad (IV)$$

are preferably reacted with alkenes B having at least 2 carbon atoms which are optionally substituted by fluorine, chlorine or bromine atoms or cyano groups, in the presence of a transition metal catalyst, in which e is 2 or 3, and $R^1$, X, b and c have the above meanings.

In a preferred embodiment, the mono- and dialkylsilanes of the general formula (II) are prepared in the same reactor in which the process according to the invention for the preparation of the di- and trialkylsilanes of the general formula (I) is carried out (one-pot reaction). Preferably, the mono- and dialkylsilanes of the general formula (II) are not isolated, but are reacted directly with alkene A.

However, the silanes of the general formula (II) can also be prepared by organometallic alkylation of chloro- or alkoxysilanes of the general formula $$X_{c+1}SiH_a$$

or by hydride transfer to alkylsilanes of the general formula $$R^1_bSiX_{c+1}$$

in which $R^1$, x, a, b and c have the above meanings.

In the case of the one-pot reaction, for the preparation of the di- and trialkylsilanes of the general formula (I), the activator of the general formula (III) and then the silane of the general formula (IV) can be metered into the alkenes A and B, which have been initially introduced into the reaction vessel and already contain the transition metal catalyst in dissolved form.

However, the reverse procedure can also be followed, and alkene A and then alkene B or first alkene B and then alkene A can be metered into the silane of the general formula (IV), which has been initially introduced into the reaction vessel.

Preferably, the activator of the general formula (III) is initially introduced into the reaction vessel and the other components are then metered in. The activator can also be added during the reaction, which shortens the induction phase of the preparation of the di- and trialkylsilanes of the general formula (I) and overall leads to a significant increase in the space/time yield.

The preparation of the di- and trialkylsilanes of the general formula (I) can be easily controlled, for example in pressure tanks/stirred vessels, via the internal temperature or the heat balance or simply via the particular internal pressure. The pressure which can be measured in the gas phase above the reaction solution here largely corresponds to the sum of the temperature-related partial pressures of the starting materials which have not yet reacted. In the case of particularly reactive activators, such as, for example, trichlorosilane, which accordingly have short halflives, it may be advantageous to subsequently meter them in portions into the reaction mixture, and in some cases not until during the preparation of the di- and trialkylsilanes of the general formula (I).

By metering of at least one reaction component according to the consumption, the process can easily be controlled, for example via a pressure display, and emissions and, in particular, hazardous operating states can be avoided from the beginning. This also allows completely continuous addition processes with relatively short residence times of less than 30 minutes, which are particularly reliable and economical. In the continuous process, the trihalogenosilane of the general formula (III) is metered into the reactor constantly with the other starting materials, preferably with the silane of the general formula (II).

Batch processes are preferably carried out in autoclaves. Continuous processes are carried out by separate metering of the starting materials, for example into a tube or loop reactor which can be thermostatically controlled via a heat transfer oil or other method. At the end of the continuous reactor, the virtually completely reacted mixture is passed over an overflow valve or pressure retention valve, for example, and collected in a steel tank.

In a preferred embodiment, after the hydrosilylation the reaction mixture is preferably separated by distillation. The fraction containing the silanes of the general formula (II) and the trihalogenosilane of the general formula (III) is recycled into the hydrosilylation. This fraction is preferably the first runnings. In this embodiment, the total yield of di- and trialkylsilanes of the general formula (I) is greatly increased.

Solvents are not necessary for the preparation of the di- and trialkylsilanes of the general formula (I), but can be present. In a reaction procedure controlled by metering in particular, dilution by inert solvents such as is recommended in comparable hydrosilylations for safety reasons such as the removal of heat, can be omitted. Small additions of polar solvents, such as THF or isopropanol, may be advantageous for metering of the platinum catalyst into highly nonpolar media.

In the following examples, unless stated otherwise in each case, a) all the amounts data are based on weight;

b) all the pressures are 0.10 MPa (absolute);

c) all the temperatures are 20° C.

EXAMPLES

Example 1

(according to the invention, with $HSiCl_3$ as the trihalogenosilane)

190 kg of cyclopentene and 120 kg of dichlorosilane are introduced with stirring (300 revolutions/minute) into a 500 l pressure stirred tank with a safety valve (adjusted to 30 bar). The catalyst solution (50 g of $H_2PtCl_6.6\ H_2O$, dissolved in 1 l of isopropanol) is then metered in. The contents of the reactor are heated up, and the exothermic reaction starts at about 90° C., the temperature rising to 150° C. and the pressure to 21 bar. The progress of the reaction can be seen from the drop in pressure in the reactor. After a reaction time of 2 hours at 130° C., the internal pressure is 10 bar, and 23 kg of trichlorosilane are metered in. After a further 9 hours, a second significantly exothermic reaction is detectable (increase in temperature to 153° C.). After a further 9 hours (total reaction time 21 hours) at a reaction temperature of 130–140° C., the pressure in the reactor has fallen to 4 bar. The reactor is cooled and emptied. 329 kg of crude product comprising 58.6% of dicyclopentyldichlorosilane, 12.0% of cyclopentene, 13.3% of $CpSiHCl_2$, 9.4% of $CpSiCl_3$ and only 6.7% of by-products which cannot be used further are obtained.

Example 2

(not according to the invention, with acetone as the activator)

200 kg of cyclopentene and 140 kg of dichlorosilane are initially introduced into a 500 l pressure stirred tank. The reaction is carried out analogously to Example 1, but instead of the trichlorosilane, 4 l of acetone are metered in under an internal pressure of 10 bar. After a reaction time of 15 hours, the second exothermic reaction is detectable (increase in temperature to 158° C.). After a further 7 hours (total reaction time 22 hours) at 130–140° C., the internal pressure in the reactor is 5 bar. The mixture which is now under normal pressure and has cooled to room temperature is taken off via the bottom valve. 342 kg of crude product comprises 57.6% of dicyclopentyldichlorosilane, 13.0% of cyclopentene, 14.4% of $CpSiHCl_2$, 3.3% of $CpSiCl_3$ and 11.7% of by-products which cannot be used further (for example, cyclopentylpropylSiCl2).

Example 3

(according to the invention with recycling of the first runnings)

60 kg of distillation first runnings, comprising chiefly $CpSiCl_3$ (about 35%) and $CpSiHCl_2$ (about 60%), 130 kg of dichlorosilane and 195 kg of cyclopentene are initially introduced into a 500 l pressure stirred tank. As described in Example 1, the catalyst is added and the contents of the reactor are heated up, the reaction starting and a maximum internal temperature of 164° C. and pressure of 18 bar being reached. The mixture is then kept at about 130° C. (internal pressure of 9 bar). After a reaction time of 13 hours, the second exothermic reaction can be detected by the increase in temperature to 161° C. After a total reaction time of 25 hours under an internal pressure of 4 bar at 132° C., the contents of the tank are cooled. 380 kg of crude product with a dicyclopentyldichlorosilane content of 70.8% are obtained. According to the gas chromatogram, the product further comprises 3.4% of cyclopentene, 9.5% of $CpSiHCl_2$, 6.0% of $CpSiCl_3$ and 10.3% of by-products which cannot be used further.

Distillation:

Three mixtures with crude product and fraction 2 of the preceding distillation charge are combined in a distillation unit with a column and 1500 l still and are subjected to discontinuous distillation. The reservoir is slowly heated up under normal pressure until a reflux of 150 l/hour is obtained. Distillate (low-boiling constituents, such as cyclopentene and $SiCl_4$) is then removed until a bottom temperature of 130° C. is reached. The reservoir is cooled to 25° C., a vacuum of less than 50 mbar is slowly established and the mixture is heated up again. The distillate obtained is removed in several fractions. Fraction 1 (amount 180 kg, pressure 50 mbar, temperature 30–100° C.) corresponds to the first runnings and is employed again in the reaction (see above), fraction 2 (180 kg, 1 mbar, 100–110° C.) is employed again in the following distillation charge, and fraction 3 (820 kg, 1 mbar, 111–116° C.) is the main runnings containing the target product dicyclopentyldichlorosilane in a purity of >95%.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of di- and trialkylsilanes of the general formula (I)

$$R_a R^1_b SiX_c \qquad (I)$$

by hydrosilylation, comprising reacting mono- or dialkylsilanes of the general formula (II)

$$R^1_b SiH_a X_c \qquad (II)$$

with alkenes A having at least 3 carbon atoms, which are optionally substituted by fluorine, chlorine, or bromine, or cyano groups, in the presence of a transition metal catalyst and a trihalogenosilane of the general formula (III)

$$R^2 SiY_3 \qquad (III)$$

as an activator,
wherein, in the above general formulae (I) to (II),

R is a branched or cyclic hydrocarbon radical having at least 3 carbon atoms, optionally substituted by fluorine, chlorine, or bromine, or cyano groups, $R^1$ is an alkyl radical optionally substituted by fluorine, chlorine, or bromine, or cyano groups, $R^2$ is a hydrogen atom, or an alkyl radical optionally substituted by fluorine, chlorine, or bromine, or cyano groups, X is fluorine, chlorine, or bromine, or an alkoxy radical having 1 to 18 carbon atoms optionally substituted by fluorine, chlorine, or bromine, or cyano groups, Y is fluorine, chlorine or bromine, a is 1 or 2, b is 1 or 2, and c is 1 or 2.

2. The process as claimed in claim 1, in which the alkenes A are branched or cyclic and have up to 18 carbon atoms.

3. The process as claimed in claim 1, in which the radical $R^1$ has at most 18 carbon atoms.

4. The process as claimed in claim 2, in which the radical $R^1$ has at most 18 carbon atoms.

5. The process as claimed in claim 1, in which the radical $R^2$ has at most 18 carbon atoms.

6. The process as claimed in claim 2, in which the radical $R^2$ has at most 18 carbon atoms.

7. The process as claimed in claim 3, in which the radical $R^2$ has at most 18 carbon atoms.

8. The process as claimed in claim 4, in which the radical $R^2$ has at most 18 carbon atoms.

9. The process as claimed in claim 1, in which Y is a chlorine atom.

10. The process as claimed in claim 2, in which Y is a chlorine atom.

11. The process as claimed in claim 3, in which Y is a chlorine atom.

12. The process as claimed in claim 4, in which Y is a chlorine atom.

13. The process as claimed in claim 1, in which the amount of activator is 0.5–30% by weight of the total mixture.

14. The process as claimed in claim 2, in which the amount of activator is 0.5–30% by weight of the total mixture.

15. The process as claimed in claim 3, in which the amount of activator is 0.5–30% by weight of the total mixture.

16. The process as claimed in claim 4, in which the amount of activator is 0.5–30% by weight of the total mixture.

17. The process as claimed in claim 1, wherein the reaction mixture is separated by distillation, and a fraction containing the silanes of the general formula (II) and the trihalogenosilane of the general formula (III) is recycled into the hydrosilylation.

* * * * *

UNITED STATES PATENT AND TRADEMARK OFFICE
CERTIFICATE OF CORRECTION

PATENT NO : 6,169,196
DATED : January 2, 2001
INVENTOR(S) : Gilbert Geisberger et al.

It is certified that error appears in the above-identified patent and that said Letters Patent are hereby corrected as shown below:

Column 7, Line 26, Claim 1, "(II)" should be (III).

Signed and Sealed this

Twenty-ninth Day of May, 2001

Attest:

NICHOLAS P. GODICI

Attesting Officer

Acting Director of the United States Patent and Trademark Office